(12) United States Patent  
Akiba

(10) Patent No.: US 9,028,066 B2  
(45) Date of Patent: May 12, 2015

(54) OPHTHALMIC APPARATUS, METHOD OF CONTROLLING THE SAME, AND STORAGE MEDIUM

(75) Inventor: Shintaro Akiba, Isehara (JP)

(73) Assignee: Canon Kabushiki Kaisha, Tokyo (JP)

( * ) Notice: Subject to any disclaimer, the term of this patent is extended or adjusted under 35 U.S.C. 154(b) by 123 days.

(21) Appl. No.: 13/398,031

(22) Filed: Feb. 16, 2012

(65) Prior Publication Data

US 2012/0218519 A1 Aug. 30, 2012

(30) Foreign Application Priority Data

Feb. 28, 2011 (JP) ................................. 2011-042657

(51) Int. Cl.  
*A61B 3/14* (2006.01)  
*A61B 3/00* (2006.01)  
*A61B 3/16* (2006.01)

(52) U.S. Cl.  
CPC ............... *A61B 3/0075* (2013.01); *A61B 3/165* (2013.01)

(58) Field of Classification Search  
CPC .............................. A61B 3/0083; A61B 3/165  
USPC .................................................. 351/208, 245  
See application file for complete search history.

(56) References Cited

U.S. PATENT DOCUMENTS

| | | | | |
|---|---|---|---|---|
| 5,116,114 A * | 5/1992 | Nakamura et al. | ............. | 351/205 |
| 6,409,343 B1 * | 6/2002 | Uchida | ........................ | 351/208 |
| 7,241,011 B2 * | 7/2007 | Baek et al. | .................... | 351/206 |
| 7,588,336 B2 * | 9/2009 | Honda et al. | .................. | 351/208 |
| 7,662,092 B2 | 2/2010 | Miyagi et al. | | |
| 8,752,962 B2 * | 6/2014 | Ono et al. | ...................... | 351/206 |
| 2001/0005260 A1 * | 6/2001 | Hara et al. | ..................... | 351/245 |
| 2004/0267093 A1 | 12/2004 | Miyagi et al. | | |
| 2008/0304011 A1 * | 12/2008 | Ng et al. | ...................... | 351/206 |
| 2009/0079939 A1 * | 3/2009 | Mimura | ....................... | 351/245 |

FOREIGN PATENT DOCUMENTS

| | | |
|---|---|---|
| JP | 08-126608 A | 5/1996 |
| JP | 08-126611 A | 5/1996 |
| JP | 3276682 B2 | 4/2002 |
| JP | 2002-369799 A | 12/2002 |
| JP | 2003-230535 A | 8/2003 |
| JP | 2004-275504 A | 10/2004 |
| JP | 3672447 B2 | 7/2005 |
| JP | 2006-130227 A | 5/2006 |
| JP | 2007-282672 A | 11/2007 |
| JP | 2008-061715 A | 3/2008 |
| JP | 4250062 B2 | 4/2009 |
| JP | 4265842 B2 | 5/2009 |
| JP | 4323209 B2 | 9/2009 |
| JP | 2009-268682 A | 11/2009 |
| JP | 2010-239999 A | 10/2010 |

* cited by examiner

*Primary Examiner* — Jordan Schwartz  
(74) *Attorney, Agent, or Firm* — Fitzpatrick, Cella, Harper & Scinto

(57) ABSTRACT

An ophthalmic apparatus includes a control unit configured to, when a manipulated value detected by a manipulated value detection unit is a first manipulated value within a predetermined range, control to move the moving unit by a fine motion operation of moving the moving unit at a low speed, and when the manipulated value is a second manipulated value outside the predetermined range, control to move the moving unit by a coarse motion operation of moving the moving unit at a speed higher than that in the fine motion operation.

7 Claims, 8 Drawing Sheets

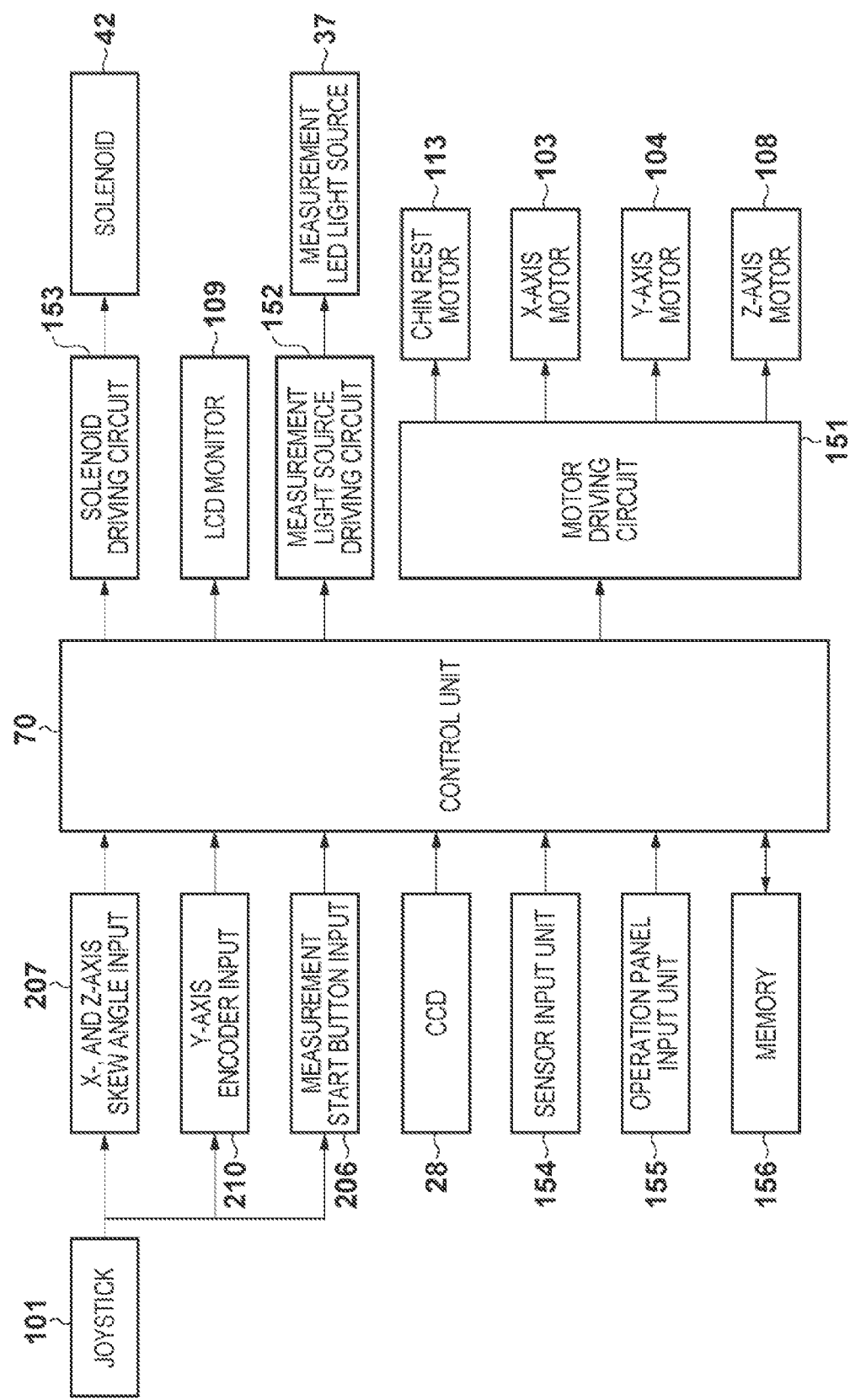

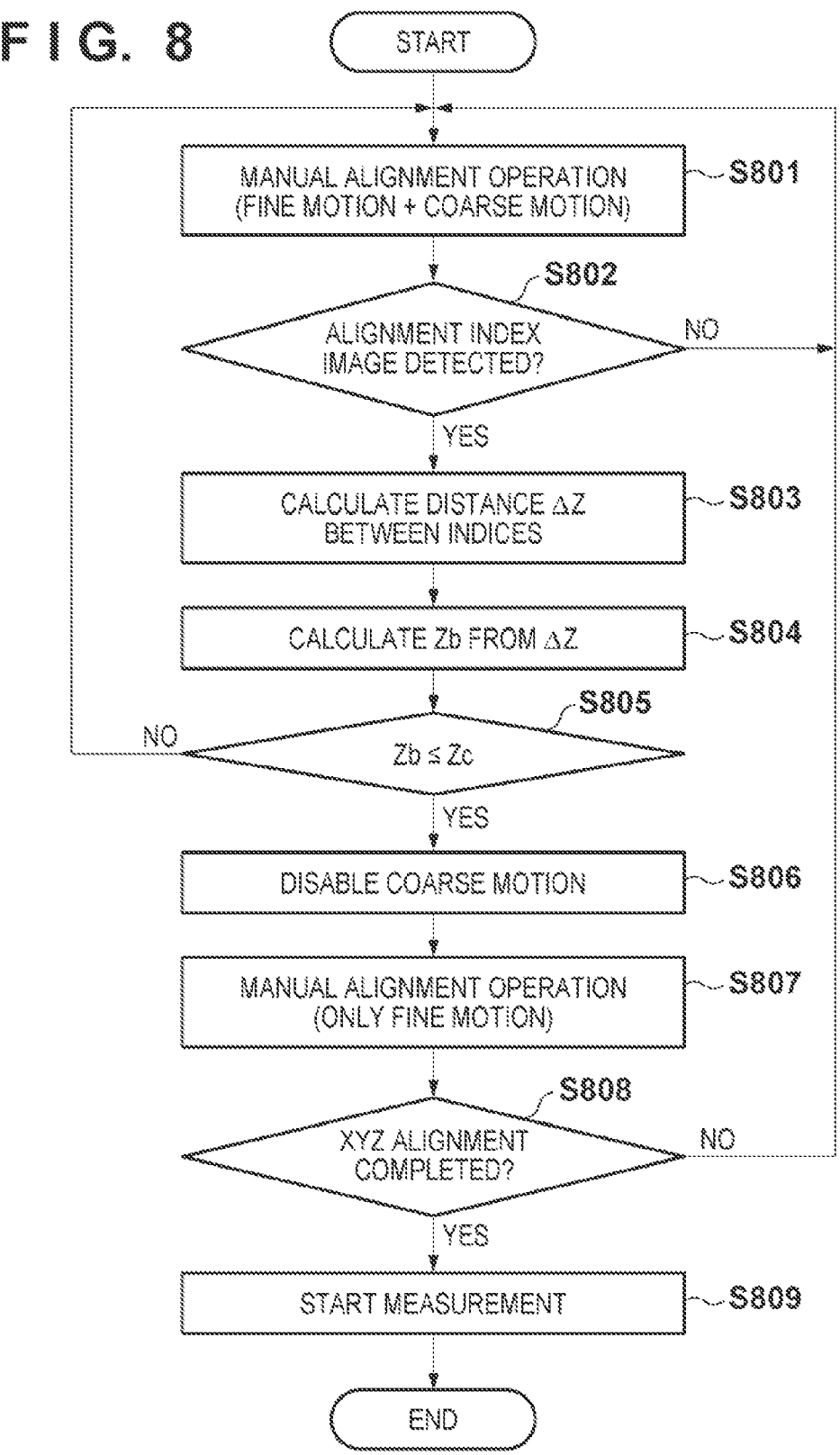

OPHTHALMIC APPARATUS, METHOD OF CONTROLLING THE SAME, AND STORAGE MEDIUM

BACKGROUND OF THE INVENTION

1. Field of the Invention

The present invention relates to an ophthalmic apparatus capable of aligning an optometric unit with an eye to be examined by manipulating an operation member to examine, observe, and capture the eye to be examined, a method of controlling the ophthalmic apparatus, and a storage medium.

2. Description of the Related Art

In an ophthalmic apparatus such as a noncontact tonometer, it is necessary to align an optometric unit with an eye to be examined so as to attain a predetermined positional relationship. There are known many products that adopt a joystick as an operation member for moving the optometric unit in the upward/downward, forward/backward, and leftward/rightward directions for this alignment adjustment. In general, the joystick of the ophthalmic apparatus can perform a "fine motion" operation of finely moving the optometric unit for fine alignment with the eye to be examined and a "coarse motion" operation of coarsely moving the optometric unit for coarse alignment.

An electric joystick has recently been developed, which implements the fine motion operation and the coarse motion operation by using electric driving and control methods (Japanese Patent Laid-Open No. 2002-369799, to be referred to as "patent literature 1" hereinafter). The joystick of patent literature 1 is mechanically configured to make the optometric unit perform "fine motion" when being manipulated in a predetermined skew angle range (for example, from −20° to +20°) and to make the optometric unit perform "coarse motion" when being manipulated beyond the predetermined skew angle range.

When aligning the optometric unit with an eye to be examined, an examiner who is inexperienced in the operation may largely move the optometric unit by erroneously manipulating the joystick into the coarse motion range against his/her intention. This not only prolongs the time up to completion of alignment but also may bring the optometric unit into contact with the eye to be examined, raising fears of the object. To solve the above-described problem, for example, Japanese Patent No. 03672447 (to be referred to as "patent literature 2" hereinafter) proposes a control method of stopping Z (forward/backward direction) direction movement until alignment in the X and Y (leftward/rightward and upward/downward) directions is completed. Japanese Patent Laid-Open No. 2004-275504 (to be referred to as "patent literature 3" hereinafter) proposes a control method of reducing the speed of alignment in the X and Y directions near the eye to be examined in accordance with a predetermined weight. Japanese Patent No. 04265842 (to be referred to as "patent literature 4" hereinafter) solves the problem by changing the moving speed up to completion of alignment in accordance with the misalignment amount between the eye to be examined and the optometric unit.

However, the arrangements of patent literatures 2 and 3 are specialized in contriving alignment in the X and Y directions. Hence, at the time of alignment in the Z direction after alignment in the X and Y directions, the optometric unit may be moved toward the eye to be examined at a high speed. Patent literature 4 includes no detailed description about misalignment detection in the Z direction, and it is therefore difficult to control the speed in the Z direction based on the misalignment amount in the Z direction. In addition, all patent literatures 2, 3, and 4 solve the problem by compromising the original operability ensured by combining fine motion and coarse motion of the joystick.

SUMMARY OF THE INVENTION

The present invention provides an ophthalmic apparatus capable of reducing the risk of contact with an eye to be examined and reducing fears of an object.

According to one aspect of the present invention, there is provided an ophthalmic apparatus including an optometric unit configured to acquire examination information of an eye to be examined, a base having a supporting member for determining a holding position of the eye to be examined, and a moving unit configured to move the optometric unit relative to the holding position, comprising: an operation unit configured to output a signal to control an operation of the moving unit in accordance with a manipulated value of an operating rod so as to adjust a position of the optometric unit relative to the holding position; a manipulated value detection unit configured to detect the manipulated value of the operating rod; a position detection unit configured to detect the position of the optometric unit relative to the holding position; and a control unit configured to, when the manipulated value detected by the manipulated value detection unit is a first manipulated value within a predetermined range, move the moving unit by a fine motion operation corresponding to the signal, and when the manipulated value is a second manipulated value outside the predetermined range, move the moving unit by a coarse motion operation of moving the moving unit at a speed higher than that in the fine motion operation corresponding to the signal, wherein when the position of the optometric unit detected by the position detection unit relative to the holding position is closer to the holding position than a predetermined reference position, the control unit stops moving the moving unit in response to a signal corresponding to the second manipulated value input from the operation unit.

According to another aspect of the present invention, there is provided an ophthalmic apparatus including an optometric unit configured to acquire examination information of an eye to be examined, a base having a supporting member for determining a holding position of the eye to be examined, and a moving unit configured to move the optometric unit relative to the holding position, comprising: an operation unit configured to output a signal to control an operation of the moving unit in accordance with a manipulated value of an operating rod so as to adjust a position of the optometric unit relative to the holding position; a manipulated value detection unit configured to detect the manipulated value of the operating rod; a position detection unit configured to detect the position of the optometric unit relative to the holding position; and a control unit configured to, when the manipulated value detected by the manipulated value detection unit is a first manipulated value within a predetermined range, move the moving unit by a fine motion operation corresponding to the signal, and when the manipulated value is a second manipulated value outside the predetermined range, move the moving unit by a coarse motion operation of moving the moving unit at a speed higher than that in the fine motion operation corresponding to the signal, wherein when the position of the optometric unit detected by the position detection unit relative to the holding position is closer to the holding position than a predetermined reference position, the control unit controls a moving speed of the moving unit to move the moving unit at a speed lower than that in the coarse motion operation in response to a signal corresponding to the second manipulated value input from the operation unit.

According to the present invention, a coarse motion operation caused by, for example, an operation error of an examiner at the time of alignment is prevented so as to prevent contact with the eye to be examined. In addition, the probability that the optometric unit moves toward the eye to be examined at a high speed near the eye to be examined can be eliminated. It is therefore possible to reduce fears of the object.

Further features of the present invention will become apparent from the following description of exemplary embodiments (with reference to the attached drawings).

BRIEF DESCRIPTION OF THE DRAWINGS

FIG. 6 is a block diagram for explaining the arrangement of the control system of the ophthalmic apparatus according to the embodiment;

FIG. 8 is a flowchart of manual alignment of the ophthalmic apparatus according to the embodiment.

DESCRIPTION OF THE EMBODIMENTS

Figure 1:
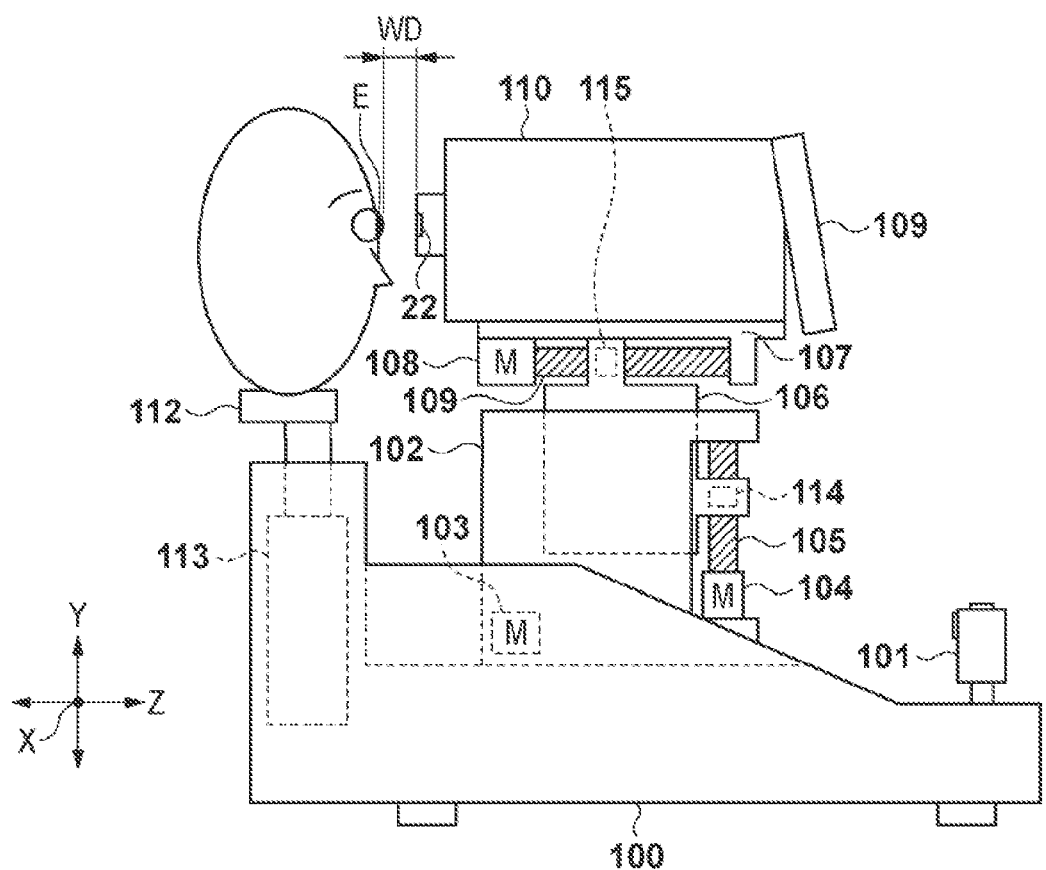
FIG. 1 is a schematic view of a noncontact tonometer that is an example of an ophthalmic apparatus according to an embodiment.

An ophthalmic apparatus according to an embodiment of the present invention will be described in detail with reference to the accompanying drawings. The schematic arrangement of a noncontact tonometer that is an example of the ophthalmic apparatus will be explained with reference to FIG. 1. This noncontact tonometer includes a base 100 having a face rest portion 112 for supporting the face of an object, a driving unit 116 and a joystick 101 serving as an operation member both of which are provided on the base 100, and an optometric unit 110 attached on the driving unit 116. The optometric unit 110 acquires the examination information of an eye to be examined. The face rest portion 112 functions as a supporting member for determining the holding position of the eye to be examined. The driving unit 116 includes driving mechanisms corresponding to the respective axes to move the optometric unit 110 in the X, Y, and Z directions.

[Movement in X-Axis Direction]

A frame 102 can move in the leftward/rightward direction (the direction perpendicular to the drawing surface; to be referred to as the X-axis direction hereinafter) relative to the base 100. A driving mechanism in the X-axis direction includes an X-axis motor 103 fixed on the base 100, a feed screw (not shown) coupled to the output shaft of the motor, and a nut (not shown) which is fixed to the frame 102 and is movable on the feed screw in the X-axis direction. The frame 102 moves in the X-axis direction through the feed screw and the nut when the X-axis motor 103 rotates.

[Movement in Y-Axis Direction]

A frame 106 can move in the upward/downward direction (to be referred to as a Y-axis direction hereinafter) with respect to the frame 102. The driving mechanism in the Y-axis direction includes a Y-axis motor 104 fixed on the frame 102, a feed screw 105 coupled to the output shaft of the motor, and a nut 114 which is fixed to the frame 106 and is movable on the feed screw in the Y-axis direction. When the Y-axis motor 104 rotates, the frame 106 moves in the Y-axis direction through the feed screw and the nut.

[Movement in Z-Axis Direction]

A frame 107 can move in the forward/backward direction (to be referred to as a Z-axis direction hereinafter) with respect to the frame 106. The driving mechanism in the Z-axis direction includes a Z-axis motor 108 fixed on the frame 107, a feed screw 109 coupled to the output shaft of the motor, and a nut 115 which is fixed to the frame 106 and is movable on the feed screw in the Z-axis direction. The frame 107 moves in the Z-axis direction through the feed screw and the nut when the Z-axis motor 108 rotates.

The optometric unit 110 for measurement is fixed on the frame 107. The optometric unit 110 includes an optical system to, for example, measure and observe the eye to be examined. An LCD monitor 109 as a display member for the observation of an eye E to be examined is provided on the end portion of the optometric unit 110 which is located on the examiner side. When measuring the eye pressure, the object places the chin on the chin rest 112 and presses the forehead against the forehead rest of a face rest frame (not shown) fixed on the base 100, thereby fixing the position of the eye to be examined.

[Joystick]

The joystick 101 that is the operation member to be used to align the optometric unit 110 with the eye E to be examined is provided on the base 100. To adjust the position of the optometric unit 110 relative to the holding position where the eye to be examined is held, the joystick 101 outputs a signal to control the operation of the driving unit 116 in accordance with a manipulated value. The examiner designates the driving direction, the driving amount, and the driving speed of the driving unit 116 by skewing the joystick 101 to align the optometric unit 110 with the eye to be examined and then executes measurement.

Figure 2:
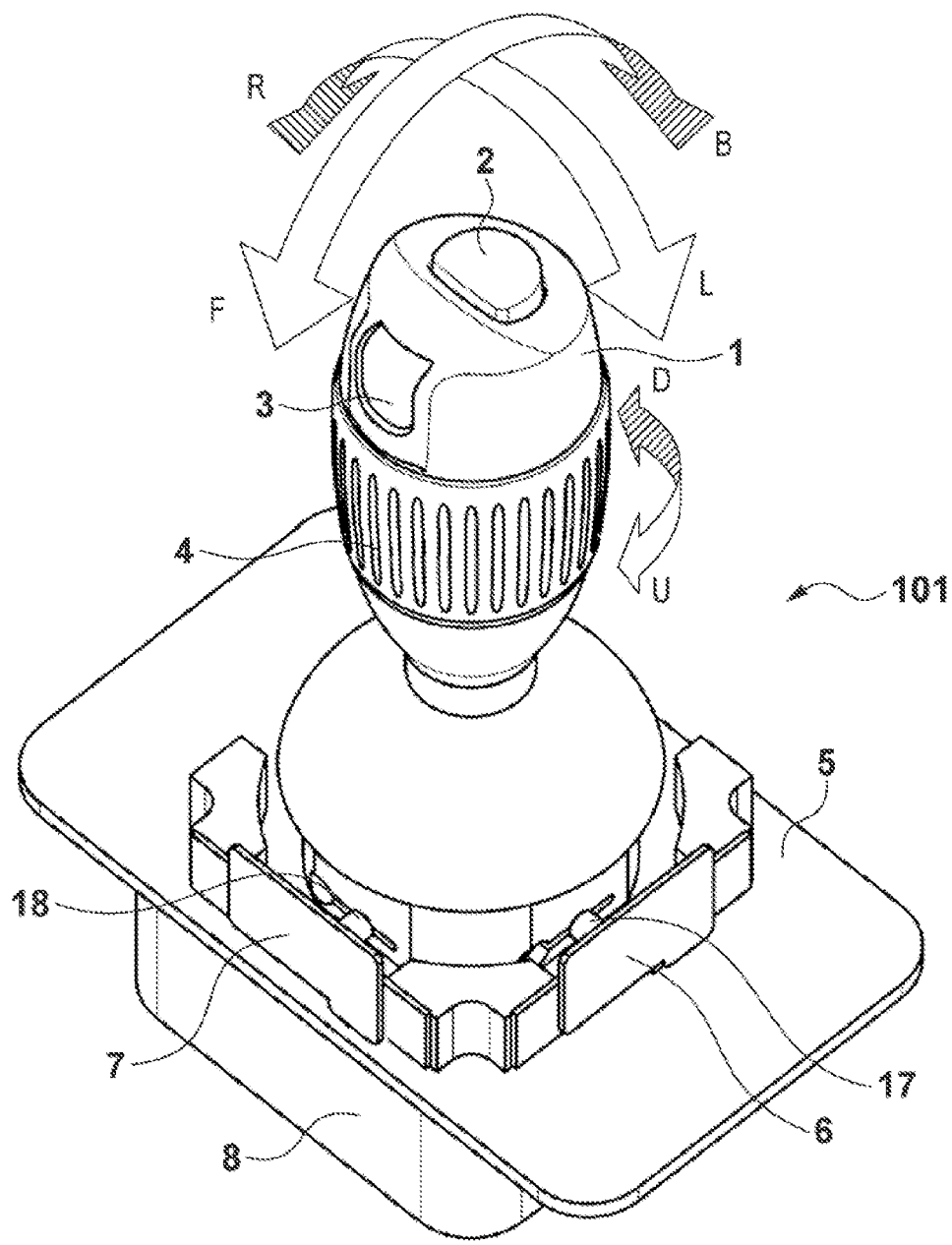
FIG. 2 is a schematic perspective view of a joystick serving as the operation member of the ophthalmic apparatus according to the embodiment.

FIG. 2 is a perspective view of the electric joystick 101 adopted in the noncontact tonometer according to the embodiment. Reference numeral 1 denotes an operating rod; 2, a measurement start button; 4, a rotating dial; 5, a bearing base: 6, a Z (forward/backward) direction position detection unit; and 7, an X (leftward/rightward) direction position detection unit. When the examiner skews the operating rod 1 in the LR (leftward/rightward) direction in FIG. 2, the optometric unit 110 moves in the eye width direction of the eye to be examined (X-axis direction). When the examiner skews the operating rod 1 in the FB (forward/backward) direction, the optometric unit 110 moves in the direction in which the unit approaches the holding position of the eye to be examined or in the direction in which the unit retreats from the holding position of the eye to be examined (Z-axis direction). When the examiner rotates the rotating dial 4 in the D or U direction, the optometric unit 110 moves in the direction in which the unit rises or falls (Y-axis direction). Details of the fine motion operation and coarse motion operation using the joystick 101 will be described later.

[Optical System]

Figure 3:
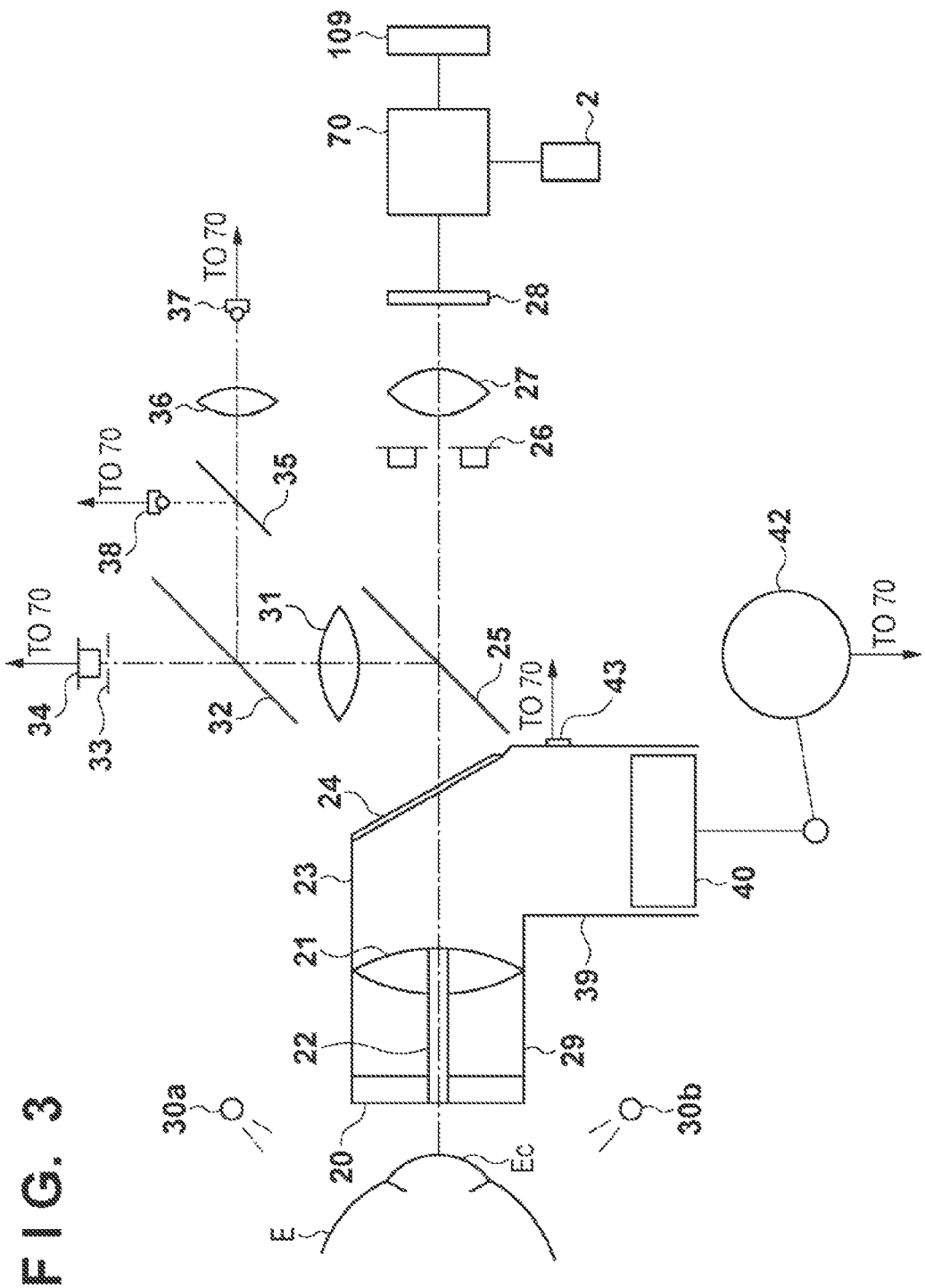
FIG. 3 is a schematic diagram of the optical system of the measurement unit of the ophthalmic apparatus according to the embodiment.

FIG. 3 is a diagram of the optical system in the optometric unit 110. A nozzle 22 is arranged on the central axis of a parallel plate glass 20 and an objective lens 21 so as to face an cornea Ec of the eye E to be examined. An air chamber 23, an observation window 24, a a dichroic mirror 25, a prism stop 26, an imaging lens 27, and an image sensor 28 are arrayed behind the objective lens 21. These components form the light receiving optical path and the alignment detection optical path of an observation optical system.

The parallel plate glass 20 and the objective lens 21 are supported by an objective lens barrel 29. Extraocular illumination light sources 30a and 30b for illuminating the eye E to be examined are arranged outside the objective lens barrel 29.

The extraocular illumination light sources 30a and 30b are illustrated on the upper and lower sides in the drawing for the descriptive convenience. In fact, the extraocular illumination light sources 30a and 30b are arranged to be perpendicular to the drawing surface so as to face each other with respect to the optical axis. A relay lens 31, a half mirror 32, an aperture 33, and a light receiving element 34 are arranged in the reflecting direction of the dichroic mirror 25. Note that the aperture 33 is arranged at a position where the cornea reflected image of a measurement light source 37 to be described later becomes conjugate at the time of predetermined deformation of the cornea Ec. The aperture 33 forms, together with the light receiving element 34, a deformation detection light receiving optical system when the cornea Ec deforms in the visual axis direction.

The relay lens 31 is designed to form a cornea reflected image having almost the same size as that of the aperture 33 at the time of predetermined deformation of the cornea Ec. A half mirror 35, a projecting lens 36, and the measurement light source 37 formed from a near-infrared LED to be used for both measurement and alignment with the eye E to be examined are arranged in the incident direction of the half mirror 32. A fixation light source 38 formed from an LED at which the object fixes the vision in examination is arranged in the incident direction of the half mirror 35.

In the air chamber 23, a piston 40 is fitted in a cylinder 39 that forms part of the air chamber 23. The piston 40 is driven by a solenoid 42. Note that a pressure sensor 43 for monitoring the internal pressure is arranged in the air chamber 23. In addition, a control unit 70 is provided to control the entire apparatus.

At the time of measurement, the fixation light source 38 is turned on. The eye E to be examined is caused to fix the vision on the fixation light source 38, and in this state, the examiner depresses the measurement start button 2. When the measurement start button 2 is depressed, the measurement light source 37 is turned on. A light beam from the measurement light source 37 changes to a parallel beam through the projecting lens 36. The light is reflected by the half mirror 32 and temporarily forms an image in the nozzle 22 through the relay lens 31. The cornea Ec of the eye E to be examined is irradiated with the formed image of the light beam.

Figure 4:
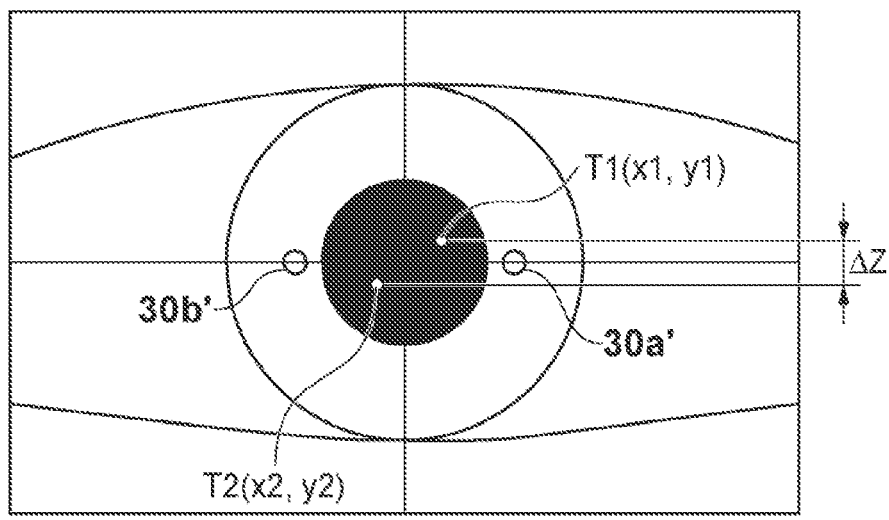
FIG. 4 is a schematic view of the display unit of the ophthalmic apparatus according to the embodiment at the time of alignment.

At the time of alignment, the prism stop 26 divides the cornea bright spot formed by the cornea Ec, as shown in FIG. 4. The image sensor 28 captures index images T1 and T2 together with the eye E to be examined illuminated by the extraocular illumination light sources 30a and 30b and bright spot images 30a' and 30b' of the extraocular illumination light sources 30a and 30b. The position difference in the y direction between the index images T1 and T2 is given by ΔZ=y1−y2. Precise alignment is performed using the index images T1 and T2 captured by the image sensor 28. FIG. 4 shows a state in which both the central axis of the nozzle and the cornea center shift.

Figure 5A:
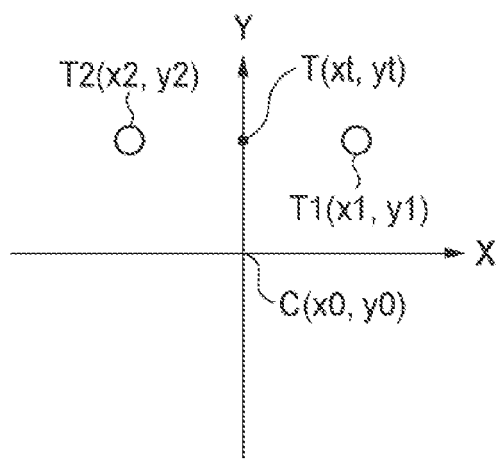
FIGS. 5A to 5D are graphs for explaining the alignment adjustment method of the ophthalmic apparatus according to the embodiment.
Figure 5B:
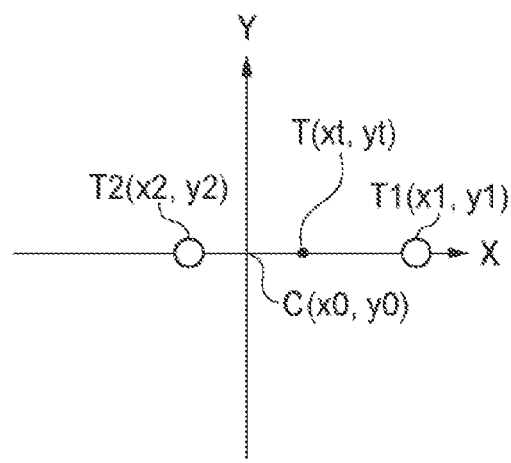

At the time of alignment, the control unit 70 calculates coordinates T1(x1, x1) and T2(x2, y2) of the two index images and center coordinates T(xt, yt) between T1 and T2. Alignment using the index images T1 and T2 will be explained here with reference to FIGS. 5A to 5D. Note that in FIGS. 5A to 5D, the cornea center is represented by an intersection C(x0, y0) of the X- and Y-axes. When the central axis of the nozzle and the cornea center shift in the Y (upward/downward) direction, y1 and y2 match each other, and x0 and xt match each other with respect to the cornea center C(x0, y0), as shown in FIG. 5A. However, y0 and yt in the Y direction are different. The driving unit 116 controls to move the optometric unit 110 in the Y direction so that the coordinate y0 equals the coordinate yt. Similarly, when the central axis of the nozzle and the cornea center shift in the X (leftward/rightward) direction, x0 and xt are different, as shown in FIG. 5B. The driving unit 116 controls to move the optometric unit 110 in the X direction so that the coordinate x0 equals the coordinate xt.

Figure 5C:
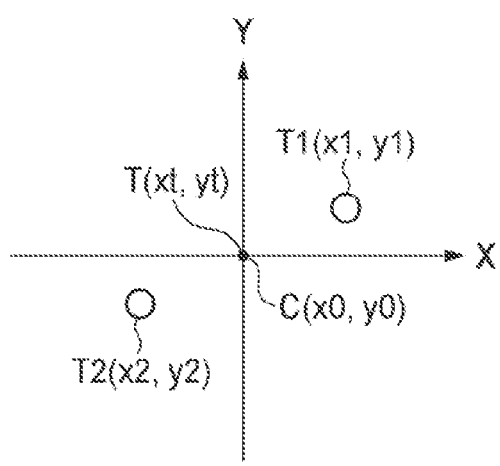
Figure 5D:
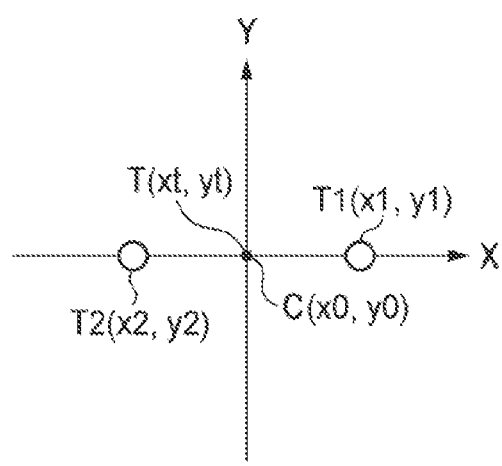

When the central axis of the nozzle and the cornea center shift in the working distance direction, that is, in the Z direction, the position of center of gravity matches the cornea center, as shown in FIG. 5C. However, x1 and x2 are different, and y1 and y2 are different. The driving unit 116 controls to move the optometric unit 110 in the Z direction so that x1 matches x2, and y1 matches y2. When the alignment is completed, the two index images T1 and T2 are arranged on the X-axis at positions equidistant from the cornea center, and the center coordinates T(xt, yt) match the cornea center C(x0, y0), as shown in FIG. 5D.

When the alignment is completed, the eye pressure is measured. The control unit 70 drives the solenoid 42. The air in the air chamber 23 is compressed by the piston 40 pushed upward by the solenoid 42 and ejected from nozzle 22 to the cornea Ec of the eye E to be examined as pulse-like air. A pressure signal detected by the pressure sensor 43 of the air chamber 23 and a received light signal from the light receiving element 34 are output to the control unit 70. The control unit 70 calculates an eye pressure value from the peak value of the received light signal and the pressure signal at that time.

[Control System]

FIG. 6 is an electric block diagram showing the control system of the noncontact tonometer according to the embodiment. An operation instruction to start the operation of aligning the optometric unit 110 with the eye E to be examined and the measurement is input from the joystick 101 to the control unit 70. A skew angle input 207 of the X- and Z-axes when the joystick 101 is skewed in the forward/backward and leftward/rightward directions, an encoder input 210 when the joystick 101 is rotated, and a measurement start button input 206 when the measurement start button is depressed are input to the control unit 70. The control unit 70 can detect the manipulated value of the joystick 101 based on the skew angle input 207 and the encoder input 210 when the joystick 101 is rotated.

A motor driving circuit 151 drives the motors (chin rest motor 113, X-axis motor 103, Y-axis motor 104, and Z-axis motor 108). A measurement light source driving circuit 152 turns on the measurement light source 37. A solenoid driving circuit 153 drives the solenoid 42. A sensor input unit 154 is an input unit that receives inputs from various kinds of sensors such as the stop position sensors of the respective axes. The sensors also include a position detection sensor that detects the position of the optometric unit 110 relative to the holding position of the eye to be examined. The control unit 70 can thus detect the position of the optometric unit 110 relative to the holding position of the eye to be examined. An operation panel input unit 155 is an input unit that receives inputs of various kinds of operations from the operation panel. A memory 156 functions as a storage unit that stores parameters to be used to save data necessary for the control of the control unit 70.

[Explanation of Control Method Using Joystick]

Figure 7:
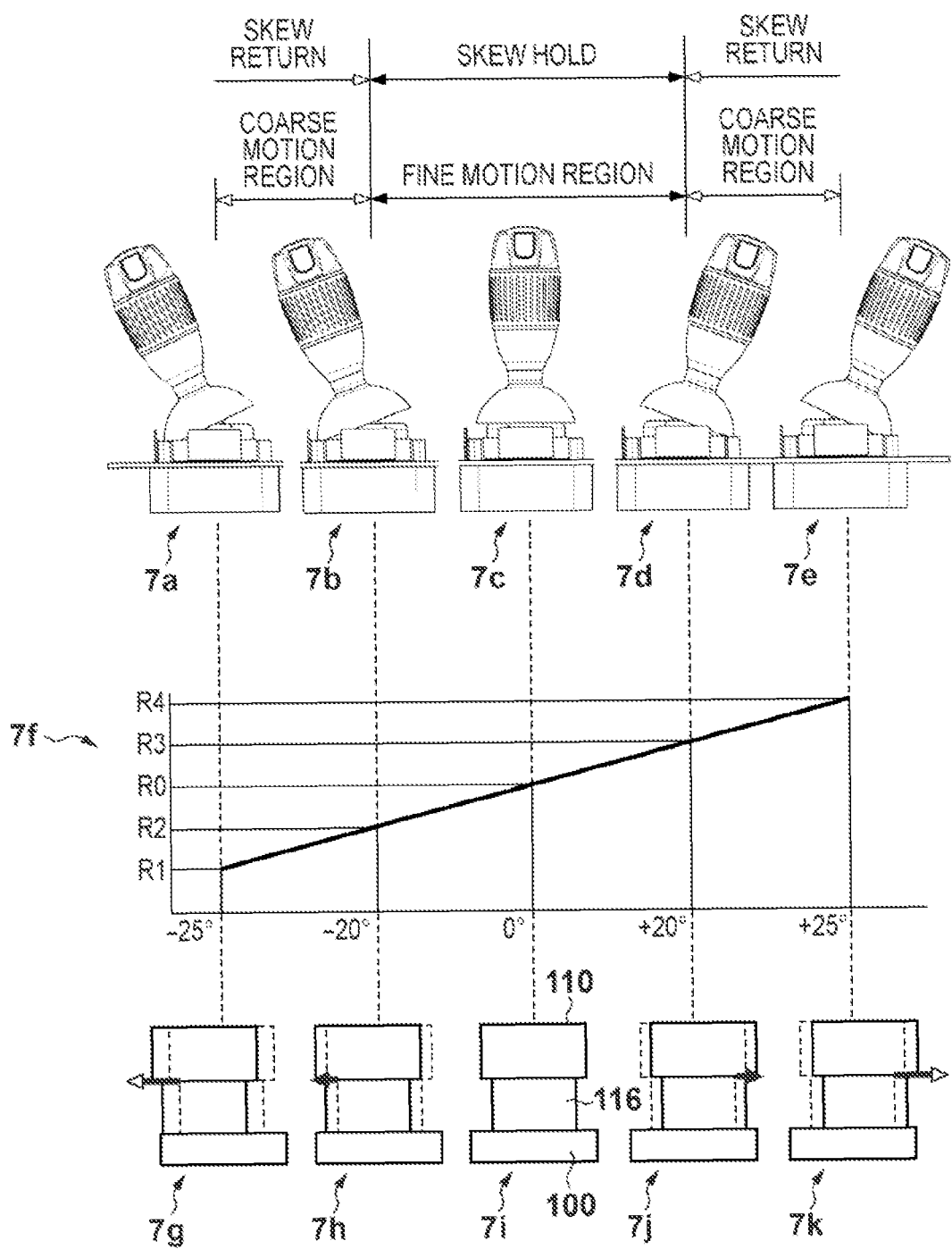
FIG. 7 is a view for explaining a control method using the joystick.

Referring to FIG. 7, 7a to 7e represent examples of the posture of the joystick 101 for a skew angle θ of the operating rod 1 in the X (leftward/rightward) direction. In FIG. 7, 7f is a graph showing the relationship between the skew angle θ and a resistance value R output from the X-direction position detection unit 7. In FIG. 7, 7g to 7k are views showing the motion of the optometric unit 110 for the skew angle θ. As for the skew angles, for example, θ1 is −25°, θ2 is −20°, θ0 is 0°, θ3 is +20°, and θ4 is +25°. Resistance values R1, R2, R0, R3, and R4 correspond to the skew angles θ1, θ2, θ0, θ3, and θ4, respectively.

[Fine Motion Operation]

In a region (first manipulated value region) where the skew angle θ of the operating rod 1 falls within the range of −20°≤θ+20° in correspondence with the resistance value from R2 to R3, the skew angle of the operating rod 1 is held. At this time, the control unit 70 controls the driving position of the X-axis motor 103 based on the output of the X-direction position detection unit 7 which changes depending on the skew angle of the operating rod 1. For example, when the examiner maintains the skew angle of the operating rod 1 within the range of −20°θ≤+20°, the control unit 70 controls the X-axis motor 103 so as to drive the optometric unit 110 within the range of, for example, −5 mm to +5 mm in proportion to the skew angle θ from the skew angle of 0°. That is, it is possible to finely align the optometric unit by the fine motion operation.

[Coarse Motion Operation]

A region where the skew angle θ of the operating rod 1 falls within the range of −25°<θ<−20° and a region where the skew angle θ falls within the range of +20°<θ<+25° (second manipulated value regions) are subjected to the coarse motion operation. In the region where the skew angle θ of the operating rod 1 falls within the range of −25°<θ<−20° in correspondence with the resistance value from R1 to R2, the control unit 70 controls the driving speed of the X-axis motor 103 based on the output of the X-direction position detection unit 7 which changes depending on the skew angle of the operating rod 1. Similarly, in the region where the skew angle θ of the operating rod 1 falls within the range of +20°<θ<+25° in correspondence with the resistance value from R3 to R4, the control unit 70 controls the driving speed of the X-axis motor 103 based on the output of the X-direction position detection unit 7 which changes depending on the skew angle of the operating rod 1.

For example, when the examiner maintains the skew angle θ within the range of −25°<θ<−20°, the control unit 70 controls the X-axis motor 103 so as to drive the optometric unit 110 at a speed of 15 mm/sec in the skew direction of the operating rod 1. Similarly, when the examiner maintains the skew angle θ within the range of +20°<θ<+25°, the control unit 70 controls the X-axis motor 103 so as to drive the optometric unit 110 at a speed of 15 mm/sec in the skew direction of the operating rod 1. That is, it is possible to largely move the optometric unit 110 by the coarse motion operation. Although the operations in the X direction have been described here, the control unit 70 can also control to enable the fine motion operation and the coarse motion operation even in the Z (forward/backward) direction based on the output of the position detection unit 6, like the X direction.

When the examiner moves the hand off the operating rod 1 in the region where the skew angle θ of the operating rod 1 falls within the range of −25°<θ<−20° (=θ2) in correspondence with the resistance value from R1 to R2, the skew angle of the operating rod 1 returns to the predetermined angle θ2. When the examiner moves the hand off the operating rod 1 in the region where the skew angle θ of the operating rod 1 falls within the range of +20° (=θ3)<θ<+25° in correspondence with the resistance value from R3 to R4, the skew angle of the operating rod 1 returns to the predetermined angle θ3. The operating rod 1 is configured to generate a return force to return from the skew angle range of the coarse motion operation to the skew angle range of the fine motion operation when the holding force of examiner on the operating rod 1 is released. This arrangement allows to eliminate the probability that the optometric unit moves toward the eye to be examined at a high speed near the eye to be examined and thus reduce fears of the object.

[Alignment Operation of Noncontact Tonometer]

The operation of the noncontact tonometer having the above-described arrangement when performing manual alignment will be described based on FIG. 8. The base 100 includes the face rest 112 as the supporting member for determining the holding position of the eye to be examined. The examiner places the chin of the object on the face rest 112 and presses the forehead of the object against the forehead rest (not shown), thereby fixing the eye to be examined. The processing starts in this state. The examiner selects the manual alignment mode and skews the joystick 101 while observing the eye E to be examined displayed on the LCD monitor 109, thereby aligning the optometric unit 110 with the eye E to be examined. At this time, when the examiner manipulates the joystick 101 within a predetermined skew angle range (from −20° to +20°), the "fine motion operation" of moving the optometric unit 110 at a low speed can be performed. In addition, when the examiner manipulates the joystick 101 beyond the predetermined skew angle range, the "coarse motion operation" of moving the optometric unit 110 at a speed higher than that in the fine motion operation can be performed (S801).

At the time of alignment, if the optometric unit 110 shifts in the Z direction relative to the eye E to be examined, both the x-position and y-position change between the index images T1(x1, y1) and T2(x2, y2), as shown in FIG. 5C. Let ΔZ=y1−y2 be the position difference in the y direction between the index images T1 and T2, Zb be the position of the optometric unit 110 in the Z (forward/backward) direction during alignment, and Za be the alignment completion target position. In this case, Zb is given by Zb=Za+KΔZ, where K is a proportionality coefficient.

When the image sensor 28 recognizes the index images T1 and T2 (YES in step S802), the control unit 70 calculates the positions of the index images T1(x1, y1) and T2(x2, y2) and the difference ΔZ=y1−y2 between the index images T1 and T2 (S803). The control unit 70 multiplies ΔZ by the predetermined proportionality coefficient K. The control unit 70 then reads out the alignment completion target position Ka stored in the memory 156, and calculates the Z-direction position Zb (Zb=Za+KΔZ) of the optometric unit 110 in the direction in which the unit approaches the eye to be examined (S804).

The control unit 70 also reads out, from the memory 156, a predetermined Z-position parameter Zc (reference position) set by the examiner in advance, and compares the Z-direction position Zb with the Z-position parameter Zc (reference position) (S805). The predetermined Z-position parameter Zc (reference position) is a position apart from the holding position of the eye to be examined by a predetermined distance to the side of the optometric unit 110.

If the Z-direction position Zb has a value larger than that of the predetermined Z-position parameter Zc (reference position) (NO in step S805), the Z-direction position Zb is located farther from the holding position of the eye to be examined than the reference position. In this case, the process returns to step S801 to continue the alignment operation in the state in which the fine motion operation and the coarse motion operation are enabled. On the other hand, upon determining in step S805 that the Z-direction position Zb has a value equal to or smaller than that of the Z-position parameter Zc (reference position) (YES in step S805), the Z-direction position Zb is located closer to the holding position of the eye to be examined than the reference position. In this case, the control unit 70 disables the coarse motion operation input from the joystick (S806). That is, even if the input signal (207, 210) from the joystick instructs the coarse motion operation, the control unit 70 controls not to send an operation signal to the motor driving circuit 151. If the position of the optometric unit 110 relative to the detected position of the eye to be examined is closer to the holding position than the predetermined reference position, the control unit 70 controls to stop the driving unit 116 for moving the optometric unit 110 in response to the input to instruct the coarse motion operation.

Even if the examiner manipulates the joystick 101 beyond the predetermined skew angle range near the eye to be examined, the optometric unit 110 is controlled to stand still without moving. At this time, when the examiner manipulates the joystick 101 within the predetermined skew angle range, the fine motion operation is enabled, and the fine motion operation can therefore be performed (S807).

The above-described control enables to do fine position adjustment by performing alignment only by fine motion of finely moving the optometric unit near the eye E to be examined, and thus improve the alignment accuracy and largely shorten the alignment time. In addition, a coarse motion operation caused by, for example, an operation error of an examiner at the time of alignment is prevented so as to prevent contact with the eye to be examined. Furthermore, the probability that the optometric unit moves toward the eye to be examined at a high speed near the eye to be examined can be eliminated. It is therefore possible to reduce fears of the object.

When the coarse motion operation is disabled, the disabled state of the coarse motion operation set by the control unit 70 is displayed at a predetermined position of the LCD monitor 109. This allows the examiner to recognize that the coarse motion operation is currently disabled and continue the alignment operation without any concern about a failure and the like. After the alignment in all the X, Y, and Z directions is completed by the alignment operation using only the fine motion (S808), the examiner depresses the measurement start button 2 to start measurement (S809).

If the alignment needs to be interrupted before completion of alignment after the coarse motion operation has been disabled, the examiner, for example, skews the joystick in the direction in which the optometric unit separates from the eye to be examined. The control unit 70 then retreats the position of the optometric unit 110 by the fine motion operation until the Z-direction position Zb has a value larger than that of the Z-position parameter Zc (reference position), thereby enabling the coarse motion operation again.

In this embodiment, the Z-direction position of the optometric unit 110 is calculated using the alignment index images as the condition to disable the coarse motion operation. However, the present invention is not limited to this. Other light sources, for example, the extraocular illumination light sources 30a and 30b may be used, and the Z-position may be calculated from the degree of blur of the bright spot images 30a' and 30b' of the extraocular illumination light sources 30a and 30b. Alternatively, the Z-direction position of the optometric unit 110 may directly be detected using a sensor mechanism such as a photosensor.

In this embodiment, an arrangement has been described in which the motor driving circuit 151 is common to all axes, and the coarse motion operation for all axes is disabled under a predetermined condition. The present invention is not limited to this arrangement. Motor driving circuits may independently be arranged for the axes, and the coarse motion operation may be disabled under a predetermined condition only for a desired axis. The coarse motion operation only in one direction for a single axis may be disabled. For example, the coarse motion operation may be disabled for, out of the Z (forward/backward) direction, only the direction in which the optometric unit approaches the holding position of the eye to be examined under a predetermined condition. That is, the control unit 70 can also control the operation of the Z-axis motor 108 so as to stop moving the optometric unit 110 in the direction in which the optometric unit approaches the holding position of the eye to be examined.

In this embodiment, the noncontact tonometer is used as the ophthalmic apparatus. However, the present invention is not limited to this and is applicable to all ophthalmic apparatuses such as an eye refractive power measuring apparatus, a fundus camera, and OCT that need to align the optometric unit with the eye to be examined using a joystick or the like.

According to this embodiment, fine position adjustment can easily be done in alignment using only fine motion near the eye to be examined. This allows to improve the alignment accuracy and shorten the alignment time. In addition, preventing the coarse motion operation caused by, for example, an operation error of the examiner at the time of alignment enables to prevent contact with the eye to be examined. Furthermore, since the probability that the optometric unit moves toward the eye to be examined at a high speed near the eye to be examined is eliminated, fears of the object can be reduced.

(Modification)

In the above-described embodiment, the coarse motion operation is disabled under a predetermined condition to stop the operation at the time of coarse motion. However, the present invention is not limited to this arrangement. Instead, the moving speed of the driving unit 116 may be controlled such that the optometric unit 110 moves at a moving speed lower than that in the coarse motion operation. The control unit 70 may control the moving speed of the driving unit 116 such that the optometric unit moves at a moving speed lower than that in the coarse motion operation, for example, the moving speed at the time of fine motion operation or a speed lower than it. In this case, for example, a linear speed pattern that changes the speed linearly with respect to time is set as the speed pattern (first speed pattern) in the coarse motion operation. In addition, a speed pattern (second speed pattern) to implement a lower moving speed than that in the coarse motion operation is set. As the second speed pattern, for example, a linear speed pattern having a slope smaller than that of the linear speed pattern as the first speed pattern can be set. Alternatively, a speed pattern defined by a nonlinear function such as a parabola that is a function in the region where the speed is lower than the linear speed pattern (first speed pattern) may be set as the second speed pattern. The control unit 70 can control the moving speed of the optometric unit 110 to a moving speed lower than that in the coarse motion operation by switching the first speed pattern to the second speed pattern.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-042657, filed Feb. 28, 2011, which is hereby incorporated by reference herein in its entirety.

What is claimed is:

1. An ophthalmic apparatus including (a) an optometric unit configured to acquire examination information of an eye to be examined, (b) a base having a supporting member for determining a holding position of the eye to be examined, and (c) a moving unit configured to move the optometric unit relative to the holding position, the apparatus comprising:
an operation unit configured to output a signal to control an operation of the moving unit in accordance with a manipulated value of an operating rod so as to adjust a position of the optometric unit relative to the holding position;
a manipulated value detection unit configured to detect the manipulated value of the operating rod;
a position calculation unit configured to calculate the position of the optometric unit relative to the holding position based on a difference between coordinate values of index images on a cornea of the eye; and
a control unit configured to, when the manipulated value detected by said manipulated value detection unit is a first manipulated value within a predetermined range, move the moving unit by a fine motion operation corresponding to the signal, and when the manipulated value is a second manipulated value outside the predetermined range, move the moving unit by a coarse motion operation of moving the moving unit at a speed higher than that in the fine motion operation corresponding to the signal,
wherein when the position of the optometric unit calculated by said position calculation unit relative to the holding position is closer to the holding position than a predetermined reference position, said control unit (a) allows moving the moving unit in any direction in response to a first signal corresponding to the first manipulated value input from said operation unit and (b) stops moving the moving unit in a direction in which the optometric unit approaches the holding position in response to a second signal corresponding to the second manipulated value input from said operation unit.

2. The apparatus according to claim 1, wherein said control unit causes a display unit to display that the moving unit is stopped in its coarse movement in response to the signal corresponding to the second manipulated value input from said operation unit when the position of the optometric unit calculated by said position calculation unit relative to the holding position is calculated to be closer to the holding position than a predetermined reference position.

3. An ophthalmic apparatus including (a) an optometric unit configured to acquire examination information of an eye to be examined, (b) a base having a supporting member for determining a holding position of the eye to be examined, and (c) a moving unit configured to move the optometric unit relative to the holding position, the apparatus comprising:
an operation unit configured to output a signal to control an operation of the moving unit in accordance with a manipulated value of an operating rod so as to adjust a position of the optometric unit relative to the holding position;
a manipulated value detection unit configured to detect the manipulated value of the operating rod;
a position calculation unit configured to calculate the position of the optometric unit relative to the holding position based on a difference between coordinate values of index images on a cornea of the eye; and
a control unit configured to, when the manipulated value detected by said manipulated value detection unit is a first manipulated value within a predetermined range, move the moving unit by a fine motion operation corresponding to the signal, and when the manipulated value is a second manipulated value outside the predetermined range, move the moving unit by a coarse motion operation of moving the moving unit at a speed higher than that in the fine motion operation corresponding to the signal,
wherein when the position of the optometric unit calculated by said position calculation unit relative to the holding position is closer to the holding position than a predetermined reference position, said control unit controls a moving speed of the moving unit to move the moving unit in response to a first signal corresponding to the first manipulated value input from said operation unit at a speed lower than that in the coarse motion operation in a direction in which the optometric unit approaches the holding position in response to a second signal corresponding to the second manipulated value input from said operation unit.

4. The apparatus according to claim 3, wherein when controlling the moving speed of the moving unit to move the moving unit at the speed lower than that in the coarse motion operation, said control unit controls the moving speed of the moving unit by switching a first speed pattern for moving the moving unit in the coarse motion operation to a second speed pattern having a speed lower than that of the first speed pattern.

5. A method of controlling an ophthalmic apparatus including (a) an optometric unit configured to acquire examination information of an eye to be examined, (b) a base having a supporting member for determining a holding position of the eye to be examined, (c) a moving unit configured to move the optometric unit relative to the holding position, (d) an operation unit configured to output a signal to control an operation of the moving unit in accordance with a manipulated value of an operating rod so as to adjust a position of the optometric unit relative to the holding position, and (e) a manipulated value detection unit configured to detect the manipulated value of the operating rod, the method comprising:
a position calculation step of calculating the position of the optometric unit relative to the holding position based on a difference between coordinate values of index images on a cornea of the eye; and
a control step of, when the manipulated value detected by the manipulated value detection unit is a first manipulated value within a predetermined range, moving the moving unit by a fine motion operation corresponding to the signal, and when the manipulated value is a second manipulated value outside the predetermined range, moving the moving unit by a coarse motion operation of moving the moving unit at a speed higher than that in the fine motion operation corresponding to the signal, wherein in the control step, when the position of the optometric unit calculated in the position calculation step relative to the holding position is closer to the holding position than a predetermined reference position, (a) moving of the moving unit is allowed in any direction in response to a first signal corresponding to the first manipulated value input from the operation unit and (b) moving of the moving unit is stopped in a direction in which the optometric unit approaches the holding position in response to a second signal corresponding to the second manipulated value input from the operation unit.

6. A method of controlling an ophthalmic apparatus including (a) an optometric unit configured to acquire examination information of an eye to be examined, (b) a base having a supporting member for determining a holding position of the eye to be examined, (c) a moving unit configured to move the optometric unit relative to the holding position, (d) an operation unit configured to output a signal to control an operation of the moving unit in accordance with a manipulated value of an operating rod so as to adjust a position of the optometric unit relative to the holding position, and (e) a manipulated value detection unit configured to detect the manipulated value of the operating rod, the method comprising:

a position calculation step of calculating the position of the optometric unit relative to the holding position based on a difference between coordinate values of index images on a cornea of the eye; and a control step of, when the manipulated value detected by the manipulated value detection unit is a first manipulated value within a predetermined range, moving the moving unit by a fine motion operation corresponding to the signal, and when the manipulated value is a second manipulated value outside the predetermined range, moving the moving unit by a coarse motion operation of moving the moving unit at a speed higher than that in the fine motion operation corresponding to the signal, wherein in the control step, when the position of the optometric unit calculated in the position calculation step relative to the holding position is closer to the holding position than a predetermined reference position, a moving speed of the moving unit is controlled to move the moving unit in response to a first signal corresponding to the first manipulated value input from the operation unit at a speed lower than that in the coarse motion operation in a direction in which the optometric unit approaches the holding position in response to a second signal corresponding to the second manipulated value input from the operation unit.

7. A non-transitory computer-readable storage medium storing a program that causes a computer to function as each unit of an ophthalmic apparatus according to claim 1.

* * * * *